United States Patent
Kisaka et al.

(10) Patent No.: US 7,176,351 B2
(45) Date of Patent: Feb. 13, 2007

(54) POTATOES HAVING AN INCREASED YIELD OF STARCH PER PLANT BODY AND METHOD FOR PRODUCING THE SAME

(75) Inventors: Hiroaki Kisaka, Kawasaki (JP); Shuichi Yanagisawa, Okayama (JP); Tetsuya Miwa, Kawasaki (JP); Ai Akiyama, Kawasaki (JP)

(73) Assignee: Ajinomoto Co., Inc., Tokyo (JP)

( * ) Notice: Subject to any disclaimer, the term of this patent is extended or adjusted under 35 U.S.C. 154(b) by 0 days.

(21) Appl. No.: 10/970,987

(22) Filed: Oct. 25, 2004

(65) Prior Publication Data

US 2005/0114925 A1 May 26, 2005

(30) Foreign Application Priority Data

Oct. 30, 2003 (JP) .............................. 2003-370655

(51) Int. Cl.
*A01H 5/00* (2006.01)
*C12N 5/04* (2006.01)
*C12N 15/29* (2006.01)
*C12N 15/82* (2006.01)

(52) U.S. Cl. ............... 800/290; 800/317.2; 800/284; 800/278; 435/69.1; 435/468; 435/320.1; 536/23.1; 536/23.6

(58) Field of Classification Search ............... None
See application file for complete search history.

(56) References Cited

U.S. PATENT DOCUMENTS

| | | | | |
|---|---|---|---|---|
| 6,103,893 A | * | 8/2000 | Cooke et al. ............... | 536/102 |
| 2003/0177520 A1 | * | 9/2003 | Yanagisawa et al. ....... | 800/278 |
| 2004/0045055 A1 | * | 3/2004 | Neff ............................ | 800/287 |

FOREIGN PATENT DOCUMENTS

| DE | 197 00 334 | 7/1998 |
|---|---|---|
| RU | 2196145 | 1/2003 |
| WO | 98/58069 | 12/1998 |

OTHER PUBLICATIONS

Yang et al 2001. PNAS 98:11438-11443 p. 11443.*
Reichmann et al 2000. Current Opinion in Plant Biology 3:423-434, p. 427.*
Yanagisawa, S., "Dof1 and Dof2 transcription factors are associated with expression of multiple genes involved in carbon metabolism in maize," The Plant Journal 2000;21(3):281-288.
Search Report for French Appl. No. 0411393 (May 30, 2005).
Offical Action for Russian Appl. No. 2004131495 (Jun. 21, 2005).
U.S. Appl. No. 11/059,687, filed Feb. 17, 2005, Kisaka et al.
Beaujean, A., et al., "Integration and expression of Sorghum C4 phosphoenolpyrvate carboxylase and chloroplastic NADP+-malate dehydrogenase separately or together in C3 potato plants", Plant Science, 2001, vol. 160, pp. 1199-1210.
Veramendi, J., et al., "Antisense Repression of Hexokinase 1 Leads to an Overaccumulation of Starch in Leaves of Transgenic Potato Plants But Not to Significant Changes in Tuber Carbohydrate Metabolism", Plant Physiology, Sep. 1999, vol. 121, pp. 123-133.
Riesmeier, J. W., et al., "Evidence for an essential role of the sucrose transporter in phloem loading and assimilate partitioning", The EMBO, 1994, vol. 13, No. 1, pp. 1-7.
Yanagisawa, S., et al., "Involvement of Maize Dof Zinc Finger Proteins in Tissue-Specific and Light-Regulated Gene Expression", The Plant Cell, Jan. 1998, vol. 10, pp. 75-89.
Agarie, S., et al., "Overexpression of C4 PEPC caused O2-insensitive photosynthesis in transgenic rice plants", Plant Science, 2002, vol. 162, pp. 257-265.
Dordon, W., et al., "A modified method for routine Agrobacterium-mediated transformation of in vitro grown potato microtubers", Plant Cell Reporters, 1993, vol. 12, pp. 324-327.

* cited by examiner

*Primary Examiner*—David T. Fox
*Assistant Examiner*—Brent T Page
(74) *Attorney, Agent, or Firm*—Cermak & Kenealy, LLP; Shelly Guest Cermak

(57) ABSTRACT

The present invention provides potatoes having a tuber yield of potatoes per plant higher than that of non-transformed potatoes cultivated under the same conditions, wherein a gene encoding DNA linking protein belonging to Dof family is introduced in the potatoes. The present invention also provides a method for producing potatoes having a tuber yield of potatoes per plant body higher than that of non-transformed potatoes cultivated under the same conditions, comprising introducing a gene encoding a DNA linking protein belonging to Dof family into the potatoes, and expressing said gene in the potatoes.

6 Claims, 2 Drawing Sheets

POTATOES HAVING AN INCREASED YIELD OF STARCH PER PLANT BODY AND METHOD FOR PRODUCING THE SAME

BACKGROUND OF THE INVENTION

1. Field of the Invention

The present invention relates to potatoes and potato plants having a higher starch content per plant body by increasing both the tuber, or underground portion, of the potato plant and the starch content per unit weight of the tuber. The present invention also relates to a method for producing potatoes and a method for producing starch from potatoes.

2. Brief Description of the Related Art

Carbohydrates in plants are mainly present in the form of starch. In Japan, the use of potatoes as a starting material for starch is the highest at about 40%. The use of potatoes as food and in processed foods is 25% and 10%, respectively. The consumption of starch is increasing each year, while the crop yield of potatoes is decreasing. Therefore, there is a need in the art to increase the starch content of potato tubers.

In light of this need, attempts have been made to improve the capacity of carbon dioxide assimilation, as well as the capacity to accumulate substances in the reserve organ so as to synthesize and accumulate an excess amount of saccharides. However, even if the starch content of the tubers can be increased, the amount of tubers is often reduced. The amount of starch calculated per plant body can be increased in only a few cases.

For example, Beaujean et al. introduced C4-phosphoenolpyrvate carboxylase (C4-PEPC) from sorghum and NADP-dependent malate dehydrogenase gene into potatoes in an attempt to increase the carbon dioxide assimilation efficiency of the potatoes. Although an increase in the amount of protein and an increase in the protein activity was observed, the starch content of the tubers did not change (Beaujean et al., Plant Science 160, 1199–1210, 2001). Veramendi et al. introduced the hexokinase 1 gene in an antisense direction into potatoes in an attempt to increase the starch content and succeeded in reducing the hexokinase activity of the potatoes 22% as compared to wild-type strains. As a result, no change in the starch content of the tubers was observed, while the starch content of leaf tissue could be increased 3-fold (Veramendi et al., Plant Physiology 121, 123–134, 1999). When the sucrose transporter gene was introduced in an antisense direction, the yield of tubers was greatly reduced, although the starch content of the leaf tissue was increased 5-fold and thus, starch production could not be increased (Riesmeier J W et al., The EMBO J, 13, 1–7, 1994). Thus, it is difficult to increase starch content of potatoes and the overall yield of tubers thereof at the same time. Therefore, there are no reports to date that the amount of starch per plant body can be increased.

SUMMARY OF THE INVENTION

The present invention provides a transformed potato plant and methods of using it to produce transformed potato tubers, as well as starch.

An object of the present invention is to provide a potato produced by a potato plant, wherein said potato plant is transformed with a gene encoding a DNA linking protein belonging to the Dof family and having a tuber yield of potatoes per plant body higher than that of a non-transformed potato plant cultivated under the same conditions.

It is a further object of the present invention to provide a potato as stated above, wherein the gene encoding said DNA linking protein is maize Dof1 gene.

It is a further object of the present invention to provide a potato plant having a starch content in the tuber portion higher than that of a non-transformed potato plant cultivated under the same conditions, wherein a gene encoding a DNA linking protein belonging to the Dof family is introduced into the potato plant.

It is a further object of the present invention to provide the potato plant as stated above, wherein said gene encoding the DNA linking protein belonging to the Dof family is maize Dof1 gene.

It is a further object of the present invention to provide a potato plant having a starch content per plant body higher than that of a non-transformed potato plant cultivated under the same conditions, wherein a gene encoding a DNA linking protein belonging to the Dof family is introduced into the potato.

It is a further object of the present invention to provide the potato as described above, wherein said gene encoding DNA linking protein comprises maize Dof1 gene.

It is a further object of the present invention to provide a potato which is transformed with the gene encoding a DNA linking protein belonging to the Dof family.

It is a further object of the present invention to provide the potato as described above, wherein said gene encoding a DNA linking protein comprises maize Dof1 gene.

It is a further object of the present invention to provide a progeny of the potato as described above, wherein said gene encoding the DNA linking protein is present in said potato plant.

It is a further object of the present invention to provide a progeny of the potato as described above, wherein said gene encoding a DNA linking protein is present in said potato.

It is a further object of the present invention to provide a method for producing potatoes having a tuber yield of potatoes per plant body higher than that of non-transformed potatoes cultivated under the same conditions, comprising introducing a gene encoding a DNA linking protein belonging to the Dof family into the potatoes, and expressing said gene.

It is a further object of the present invention to provide the method as described above wherein said gene encoding a DNA linking protein comprises maize Dof1 gene.

It is a further object of the present invention to provide a method for producing potatoes having a starch content in the tuber higher than that of non-transformed potatoes cultivated under the same conditions, comprising introducing a gene encoding a DNA linking protein belonging to the Dof family into the potatoes, and expressing said gene.

It is a further object of the present invention to provide the method as described above wherein said gene encoding a DNA linking protein is maize Dof1 gene.

It is a further object of the present invention to provide a method for producing potatoes having a starch content per plant body higher than that of non-transformed potatoes cultivated under the same conditions, comprising introducing a gene encoding a DNA linking protein belonging to the Dof family into the potatoes, and expressing said gene.

It is a further object of the present invention to provide the method as described above, wherein said gene encoding a DNA linking protein comprises maize Dof1 gene.

It is a further object of the present invention to provide a method for producing starch comprising cultivating the potato of claim 1 and isolating starch from the yielded tubers.

It is a further object of the present invention to provide a potato plant comprising a tuber part and a leaf part, wherein said tuber yield is higher than that of a non-transformed potato plant, wherein a gene encoding a DNA linking protein belonging to the Dof family is introduced into the potato plant.

Figure 1:
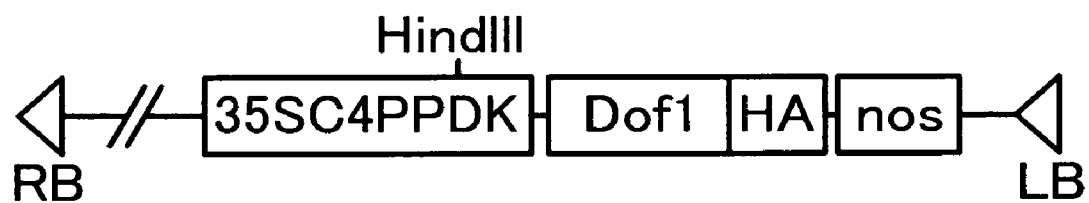
FIG. 1 is a schematic view of a Dof1-inserted part of plasmid pBI121Dof1.

Lane 1 represents a non-transformant; lane 2 represents Dof1-1; lane 3 represents Dof1-2; lane 4 represents Dof1-3; lane 5 represents Dof1-4; lane 6 represents Dof1-5; lane 7 represents Dof1-6; lane 8 represents Dof1-8; and lane 9 represents Dof1-9.

Figure 3:
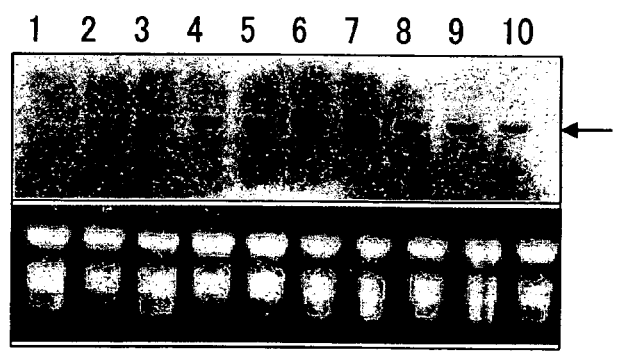

FIG. 3 represents northern analysis of the leaf tissue of the Dof1 transformed potatoes.

Lanes 1-2 represent the non-transformant; lane 3 represents Dof1-1; lane 4 represents Dof1-2; lane 5 represents Dof1-3; lane 6 represents Dof1-4; lane 7 represents Dof1-5; lane 8 represents Dof1-6; lane 9 represents Dof1 8; and lane 10 represents Dof1-9.

DESCRIPTION OF THE PREFERRED EMBODIMENTS

The object of the present invention is to provide a method for producing potatoes having increased starch content per plant body by increasing both starch content of the potato tubers and the tuber yield of potatoes for increasing the productivity of starch from potatoes.

The inventors considered that nitrogen absorption and metabolism can be activated by over-expression of transcriptional regulatory factor Dof1 gene from maize in potato cells. The transcriptional regulatory factor Dof1 gene from maize is a positive regulatory factor for phosphoenolpyruvate carboxylase gene and cytoplasmic pyruvate orthophosphoric acid dikinase gene. It is considered that by simultaneously increasing these enzymatic activities, the stream of the carbon metabolism is shifted to the amino acid synthesizing system (Japanese Patent Application No. 2002-40947). Therefore, the inventors found that when Dof1 gene is over-expressed in a plant, the amount of amino acid synthesized therein is increased and, as a result, nitrogen assimilating power is improved. Nitrogen is the most important growth restriction factor for plants and it is supposed that when nitrogen-absorbing power and nitrogen-assimilating power of a plant are improved by the introduction of Dof1 gene, the growth of the plant is accelerated and an increased amount of resources can be accumulated in the plant. In potatoes, during formation of a storage organ, or the tubers, such accumulated nutrients are supposed to be transported into the tubers by translocation to promote the tuber formation and, therefore, to increase the tuber yield. Furthermore, saccharides transported in an excess amount is converted to starch (storage form) and accumulated in a large amount in the tubers.

The inventors produced transformed potatoes wherein Dof1 gene is introduced therein and actually confirmed both an increase in the yield of the tubers and an increase in the starch content of a unit weight of the tubers at the same time.

As a result, it was confirmed that the amount of starch obtained per a plant body of potato was increased.

The DNA linking protein belonging to Dof family of the present invention may be isolated from a species of plant other than the potato. The DNA linking protein isolated from a plant other than the potato may function as a master controlling protein in the carbon feeder pathway or, in other words, as a part of group of proteins controlling a metabolic pathway to 2-oxoglutarate. In particular, the DNA linking protein may function as a protein which controls the metabolic pathway ranging from a triose to 2-oxoglutarate in the glycolysis system and subsequent TCA cycle. Dof1 from maize is preferred. Furthermore, a variant of the DNA linking protein of the present invention is also encompassed and may have deletions, replacements or additions of one or more amino acids, as long as it has the above-described function. In addition, a gene capable of hybridizing a nucleic acid molecule encoding the DNA linking protein belonging to Dof family under stringent conditions is also encompassed in the present invention.

The term "stringent conditions" as used herein indicates conditions under which so-called specific hybrids are produced. It is difficult to clearly numerate the stringent conditions because they vary depending on the GC content of each sequence, the presence or absence of the repeated sequences, and the like. The stringent conditions are, for example, conditions under which nucleic acid molecules having a high homology, for example, nucleic acid molecules having a homology of at least 65%, preferably more than 75%, even more preferably more than 85%, and most preferably more than 95%, hybridize, but nucleic acids having a lower homology do not hybridize. The stringent conditions are also such that nucleic acid molecules hybridize under a salt concentration corresponding to ordinary Southern hybridization washing conditions (60° C., 1×SSC, 0.1% SDS, preferably 0.1×SSC, 0.1% SDS).

In view of their role as the master control gene and protein, and also in view of the fact that maize Dof1 also functions in *Arabidopsis thaliana*, it is believed that even a heterologous DNA linking protein belonging to Dof family and the gene thereof will exhibit an equivalent function to that of maize Dof1 also in an intended plant. The phrase "having the function equivalent to that of maize Dof1" as used in the present invention indicates that it has a function of accelerating the transcription of phosphoenolpyruvate carboxylase gene and/or cytoplasmic pyruvate orthophosphoric acid dikinase gene.

The above-described Dof family gene or cDNA thereof can be relatively easily prepared using the published sequence information. For example, for the maize Dof1 gene, the base sequence of cDNA thereof is disclosed (Genbank accession No. X66076) (SEQ ID NOS. 1 and 2). Dof1 cDNA can be relatively easily obtained by synthesizing a PCR primer useful for amplifying a DNA encoding the protein according to the sequence thereof and then conducting RT-PCR with RNA extracted from maize leaves as the template.

According to the present invention, potatoes having an increased tuber yield and/or potatoes having an increased starch content per a unit weight of the tubers and/or potatoes having an increased amount of starch per plant body are produced by introducing a nucleic acid construct containing the maize Dof1 gene into potatoes and expressing the Dof1 gene in the transformed potatoes. According to the present invention, the preferred average weight of the cropped tubers per plant body is at least 1.2 times higher than that of cropped tubers from the non-transformed, original plant body cultured under the same conditions. The preferred starch content per unit plant body is at least 1.5 times higher than that from the non-transformed, original plant body cultured under the same conditions.

The nucleic acid constructs used in the present invention can be prepared by methods well known in the art. The molecular biological techniques for isolating the nucleic acid construct and determining the sequence thereof can be found, for example, in Sambrook et al., Molecular cloning-Laboratory manual, the second edition, Cold Spring Harbor Laboratory Press. When the gene amplification by PCR is required for preparing nucleic acid constructs usable in the present invention, the techniques therefor are disclosed in, for example, F. M. Ausubel et al. (eds.), Current Protocols in Molecular Biology, John Wiley & Sons, Inc. (1994).

The nucleic acid constructs used in the present invention typically contain promoters which are functional in the vegetable cells, such as nopaline synthase genes, 35S promoter of cauliflower mosaic virus (CaMV35S), a suitable terminator such as nopaline synthase gene terminator, other sequences required advantageous for the expression, and marker genes for selecting the transformant such as genes resistant to chemicals, e.g. kanamycin-resistant, G418-resistant and hygromycin-resistant genes.

The promoter usable for the constructs may be a constructive promoter or an organ-specific or growth stage-specific promoter. The promoter can be selected depending on the host used, necessitated expression level, organ in which the expression is particularly intended or growth stage. In a preferred embodiment of the present invention, a powerful promoter which expresses non-specifically to the organ or growth stage is used. An example of such a promoter is CaMV35S promoter. As the organ-specific promoters, phaseolin gene promoter, patatin gene promoter, etc. are used. In the most preferred embodiment of the present invention, a construct which drives the Dof1 gene with a powerful constitutive promoter such as CaMV35S promoter is used.

The method for introducing the genes in the present invention is not particularly limited. A method for introducing the genes into plant cells or plant bodies, known in the art, can be selected depending on the host. For example, in an embodiment of the present invention, a gene introduction method with *Agrobacterium* is employed. In such a transformation system, a binary vector is desirable. When *Agrobacterium* is used, a nucleic acid construct used for the transformation further contains a T-DNA region adjacent to the DNA sequence to be introduced into plant cells. In a preferred embodiment, the imported sequence is inserted between the left and right T-DNA-border sequences. Suitable design and construction of the transformed vector based on such T-DNA are well known by those skilled in the art. Conditions for infecting a plant with *Agrobacterium* having such a nucleic acid construct are also well known by those skilled in the art. For such techniques and conditions, refer to "*Model Shokubutsu no Jikken Protocol* (Experiment protocol of model plants), Edition of Rice plant and *Arabidopsis thaliana*" (a separate volume of Saibo Kokaku) edited by Shujun-sha in 1996.

In the present invention, other gene introduction methods can also be employed. Examples of gene introduction methods which can be employed herein include, for example, a method of introducing DNA into a protoplast with polyethylene glycol or calcium, a transformation method of a protoplast by electroporation and introduction via a particle gun.

The plant cells or the like thus manipulated are selected for the transformation. The selection can be conducted according to the expression of marker genes present on the nucleic acid constructs used for the transformation. For example, when the marker genes are resistant to drugs, they can be selected by culturing or growing plant cells manipulated on a medium containing a suitable concentration of an antibiotic, herbicide or the like. When the marker genes are β-glucuronidase genes or luciferase genes, activities are screened to select the transformant. When the transformant thus identified is not a plant body but a protoplast, callus, explant or the like, it is regenerated into the plant body. The regeneration can be conducted by a method selected depending on the host plant used from the methods known in the art.

The plant body thus obtained can be cultivated by an ordinary method in the art under the same conditions as those used for cultivation of the non-transformant. For identifying the transformed plant containing the nucleic acid construct of the present invention, various molecular biology techniques can be employed in addition to the above-described selection based on the marker gene. For example, Southern hybridization or PCR can be employed for detecting the recombinant DNA-inserted fraction and the structure thereof. Northern hybridization or RT-PCR can be employed for detecting and determining RNA transcription products from the introduced nucleic acid constructs.

Expression of the Dof1 gene by the transformant is evaluated by determining the amount of the Dof1 protein or the amount of mRNA. For example, the amount of Dof1 protein can be determined by a western blotting method or the like and the amount of mRNA can be determined by a northern blotting method or quantitative RT-PCR method.

After the confirmation of the expression of Dof1 gene in the transformed potatoes, the yield of the tubers and starch content of the tubers are determined. The transformed potatoes are cultured under ordinary soil culture conditions. The plant bodies used for the soil culture are seedling bodies obtained by the habituation of transformed, cultured products or microtubers induced by the tissue culture. The tubers obtained by the ordinary culture are evaluated on the basis of the number of the tubers cropped from a unit plant body and the total weight thereof. The starch content of the tubers can be determined by crushing the whole tubers, obtaining an extract from them and determining the starch content by, for example, an enzymatic method. The preparation of the plant extract and the determination of starch content can be conducted by, for example, the method of Agarie et al. (S. Agarie, Plant Science, 2002, 162, 257–265).

The weight and starch content of the cropped tubers are determined when a significant statistically difference is 5% or less using, for example, a t-test.

The sequence from the nucleic acid construct in the introduced genome may be either hemizygous and homozygous in the transformed plant. Seed potatoes are practically vegetatively bred and the introduced gene is stably transmitted to the progenies irrespective of the conjugation mode in the sequence. The seed potatoes of the obtained transformed potatoes can be multiplied and stored by ordinary methods well known in the art.

The starch can be produced from the tubers of the transformed potatoes by ordinary methods well known to those skilled in the art.

EXAMPLES

The present invention will be specifically illustrated by the following non-limiting examples.

Example 1

Integration of Maize Dof1 Gene into Plant Transformed Vector

Dof1 gene was integrated from the 35SC4PPDK-Dof1-HA plasmid (The Plant Cell 1998, 10 (Jan.), 75–89) into the plant transformation vector pBI121 (Clontech Co.) as described below.

The 35SC4PPDK-Dof1-HA plasmid includes a region from the TATA box to the translation initiation site of the maize C4 pyruvate orthophosphoric acid dikinasegene conjugated to the Dof1 cDNA, which is downstream of the Cauliflower Mosaic Virus 35S enhancer. 2 tandem molecules of phytohemagglutinin cDNA, present as an epitope-tag, conjugated to a nopaline synthase-termination site are downstream of the Dof1 region. DNA is isolated following the double cleavage by restriction enzymes XhoI and EcoRI.

Then, the XhoI-EcoRI sequence was integrated into the T-DNA region of pBI121. First, pBI121 was digested with HindIII and blunt-ended with a cloned Pfu DNA polymerase (Stratagene Co.). After linking with phosphorylated XhoI linker (Takara Shuzo Co., Ltd.) using T4 DNA ligase (Takara Shuzo Co., Ltd.), and followed by the digestion with XhoI, the linker segments were removed using gel filtration with MicroSpin Column S-300 (Amersham-Pharmacia Co.). After autocyclization with T4 DNA ligase, a plasmid with an XhoI site in the place of the HindIII site was obtained. This plasmid contained XhoI and EcoRI as unique sites. The plasmid was cleaved by XhoI and EcoRI and then the XhoI-EcoRI sequence separately prepared from 35SC4PPDK-Dof1-HA was integrated therein to form pBI121Dof1 (FIG. 1).

Example 2

Preparation of Potato Transformants

Potatoes (variety: May Queen) were transformed using the method of Gordon et al. (Plant Cell Reports, 1993, 12: 324–327). The germ-free plants produced by the shoot apex culture were rooted in MS liquid medium. 16% sucrose solution was added thereto. Microtubers were induced by culturing in the dark. The microtubers induced under germ-free conditions were peeled, cut into thin discs (microtuber discs) and used for the *Agrobacterium* infection. The microtuber discs were pre-cultured in a re-differentiation medium (MS inorganic salts, B5 vitamin, 3% sucrose, 2 mg/l zeatin, 0.1 mg/l indole acetate, 2.5 mg/l gellan gum, pH 5.8) for 24 hours.

Plasmid pBI121Dof1 was introduced into *Agrobacterium* C58C1Rif by triparental mating with *E. coli* having pBI121Dof1 and helper *E. coli* HB101/pRK203. *Agrobacterium* containing the constructed gene was inoculated on 50 mg/l kanamycin-containing YEP medium (10 g/l bactotryptone, 10 g/l yeast extract and 1 g/l glucose) and cultured under shaking conditions at 28° C. for 24 hours. The culture product was immersed in a diluted mixture of *Agrobacterium* suspension and a culture medium (MS inorganic salt, B5 vitamin, 3% sucrose, 2 mg/l zeatin, 0.1 mg/l indole acetate, 1.0 mg/l, 5'-Dimethoxy-4'-hydroxy-acetophenone, Aldrich Co., pH 5.8) and left to stand for 10 minutes. Then, the superfluous *Agrobacterium* culture liquid was wiped with a sterilized filter paper, and transplanted in the culture medium used for the pre-culture. After the co-culture at 26° C. for 48 hours (day length: 16 hours), they were transplanted in a selection medium (MS inorganic salts, B5 vitamin, 3% sucrose, 2 mg/l zeatin, 0.1 mg/l indole acetate, 50 mg/l kanamycin, 300 mg/l cefotaxime sodiume salt and 2.5 mg/l gellan gum, pH 5.8) and the culture was continued under the same conditions. The product was transplanted in the new selection medium every two weeks and, at the same time, the re-differentiated shoots were transplanted in a rooting medium (MS inorganic salts, B5 vitamin, 3% sucrose, 50 mg/l kanamycin, 100 mg/i cefotaxime sodium salt and 2.5 mg/l gellan gum, pH 5.8). The shoot apex of the rooted plant was transplanted in the new rooting medium to repeat the resistance test 3 or 4 times. 8 roots of Dof1 transformed potatoes which had a stable resistance to kanamycin were selected.

Example 3

Confirmation of Introduced Gene

DNA was extracted from the 8 potatoes selected for their resistant to kanamycin, and also the non-transformed potatoes (Honda and Hirai, 1990, Jpn Breed 40: 339–348). PCR analysis was performed using the extracted DNA, and primers of the Dof1 gene-inserted promoter and terminator:

5'-TTCCATTGCC CAGCTATCTG TCACTT-3' (SEQ ID NO. 3) and

5'-TCATCGCAAG ACCGGCAACA GGATTC-3' (SEQ ID NO. 4)

and primers for amplifying NPTII gene in the vector:

5'-CCC CTC GGT ATC CAA TTA GAG-3' (SEQ ID NO. 5) and

5'-CGG GGG GTG GGC GAA GAA CTC CAG-3' (SEQ ID NO. 6). The reaction conditions were 94° C. for 3 minutes; 94° C. for 45 seconds, 55° C. for 30 seconds, 72° C. for 90 seconds, 35 cycles; 72° C. for 10 minutes. PCR system 2400 of Perkin-Elmer Co. was used for the reaction. The PCR product was subjected to electrophoresis with 1% agarose gel (TAE buffer) and dyed with ethidium bromide.

Figure 2:
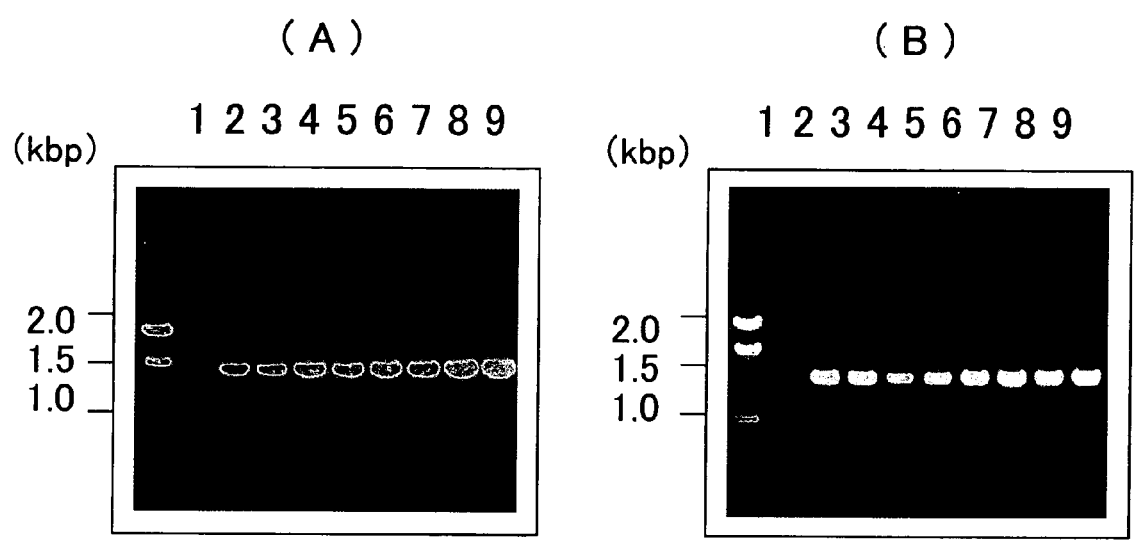
FIG. 2 shows the results of PCR analysis of Dof1 transformed potatoes, wherein A represents the PCR reaction with the Dof1 gene-containing primer, and B represents the PCR analysis with the NPTII gene-specific primer.

As a result, a Dof1 gene-containing band of about 1.5 kbp (FIG. 2a) and a band specific to the NPTII gene of about 1.1 kbp (FIG. 2b) were recognized in the selected transformed potatoes. Those bands were not recognized in the non-transformed potatoes. From these facts, it was confirmed that the Dof1 gene-containing the T-DHA domain had been introduced into the transformed potatoes.

Example 4

Confirmation of the Expression of the Introduced Gene by Northern Analysis 8 roots of transformed potatoes in which the introduction of Dof1 gene had been confirmed were subjected to northern analysis to confirm expression.

Total RNA was extracted from the leaf tissue of the transformed potatoes with RNeasy Plant mini Kit of Qiagen Co. one month after transplantation in soil. 10 μg of the extracted RNA was subjected to electrophoresis in a 1.2% agarose gel containing 18% formaldehyde, and then dyed with ethidium bromide. After blotting to a nylon membrane (HybondN+), the product was fixed with UV and hybridized. The whole length of the Dof1 gene was used as a probe. The northern blotting and the preparation of the probe were conducted with DIG-High Prime DNA Labeling and Detection Starter Kit II and PCR DIG Probe Synthesis Kit (Roche * Diagnostics Co.).

As a result, a band specific to the Dof1 gene was confirmed in the leaf tissue of the transformed potatoes (FIG. 3).

It was confirmed that the introduced Dof1 gene was transcribed and expressed in the leaf tissue of the transformed potatoes. The band specific to Dof1 gene was not recognized in the non-transformed potatoes.

Example 5

Examination of Yield of Transformed Potatoes

The yield of the transformed potatoes was examined. For the test, the germ-free plants from the transformed potatoes and non-transformed potatoes were used. After the acclimation, 0.5 kg of power soil (total nitrogen 0.2 g) was fed into a flower pot (3.5 L) and then vermiculite (nourishment-free) was added to fill the pot. Two months after the start of the culture, 0.3 kg (total nitrogen 0.12 g) of the power soil was used as the soil cover. In the course of the culture, the number of stalks was reduced to one. On the third month after transplantation, the potatoes were cropped and the weight of the above-ground part, weight of the tubers and the number of the tubers were determined.

It was found that compared to the non-transformed potatoes, the Dof1 transformed potatoes had 1.24 to 1.50 times as much weight of the above-ground part, 1.05 to 1.40 times as much weight of the tubers (below ground part) and 1.42 to 1.90 times as many tubers (Table 1).

TABLE 1

Results of the examination of yield of Dof1 transformed potatoes (n = 3)

|   | Weight of above-ground part (g) | Total weight of tubers (g) | Total number of tubers |
|---|---|---|---|
| Non-transformant | 31.02 ± 3.66 | 96.32 ± 1.60 | 6.7 ± 0.8 |
| Dof1-1 | 41.85 ± 4.47 | 122.80 ± 11.48 | 12.7 ± 1.0 |
| Dof1-2 | 38.56 ± 3.49 | 100.98 ± 8.39 | 9.7 ± 0.4 |
| Dof1-3 | 45.04 ± 0.33 | 132.29 ± 0.96 | 10.5 ± 0.2 |
| Dof1-4 | 46.38 ± 0.33 | 132.35 ± 1.95 | 12.3 ± 1.0 |
| Dof1-5 | 39.39 ± 2.77 | 109.53 ± 9.51 | 10.7 ± 1.3 |
| Dof1-6 | 39.61 ± 1.42 | 120.78 ± 13.28 | 9.5 ± 1.2 |
| Dof1-8 | 41.83 ± 1.76 | 129.02 ± 12.30 | 12.3 ± 0.2 |
| Dof1-9 | 42.43 ± 0.62 | 135.23 ± 4.27 | 12.3 ± 0.5 |

Example 6

Determination of the Starch Content of Tubers

The tubers of the transformed and non-transformed potatoes were frozen (−80° C.) immediately after harvest and kept frozen. Then, the starch content was determined. Two tubers were used in each group. The whole tubers were pulverized with liquid nitrogen. The extraction was conducted (S. Agarie et al. Plant Science 162, 2002, 257–265). The starch content was determined with F-kit starch (Roche Diagnostics Co.).

As a result, the starch content of the tubers of the Dof1 transformed potatoes was increased 1.06 to 1.53 times more than that of non-transformed potatoes. The starch content per each potato plant was increased to 2 times as high as, or even higher than, that of the non-transformed potato plant (Table 2).

TABLE 2

Starch content of Dof1 transformed potato tubers

|   | Starch content (μmol/g.F.W.) | Weight of tuber (g) | Total starch content (μmol) | ratio |
|---|---|---|---|---|
| Non-transformant | 35.71 ± 4.26 | 96.32 | 3439.52 | 1.0 |
| Dof1-1 | 48.80 ± 3.60 | 122.80 | 5993.03 | 1.7 |
| Dof1-3 | 37.80 ± 3.14 | 132.29 | 5001.13 | 1.5 |
| Dof1-4 | 42.12 ± 2.61 | 132.25 | 5570.85 | 1.6 |
| Dof1-9 | 54.91 ± 0.05 | 135.23 | 7425.48 | 2.2 |

An amino acid analysis of the tissues of leaves and stems of the plant grown under germ-free conditions was conducted to find. It was found that the total amino acid content of the Dof1 transformed potatoes was higher than that of non-transformed potatoes by 1.88 times or less.

While the invention has been described in detail with reference to preferred embodiments thereof, it will be apparent to one skilled in the art that various changes can be made, and equivalents employed, without departing from the scope of the invention. Each of the aforementioned documents, as well as the foreign priority document, JP2003-370655, is incorporated by reference herein in its entirety.

SEQ ID NO. 1: Base sequence of cDNA of maize Dof1 gene

SEQ ID NO. 2: Sequence of amino acids encoding cDNA of maize Dof1 gene

SEQ ID NOS. 3 and 4: Primers in promoter part and terminator part in which Dof1 gene was inserted SEQ ID NOS. 5 and 6: Primers for amplifying NPTII gene in the vector.

What is claimed is:

1. A method for producing a potato plant which bears potatoes, wherein said plant has a tuber yield of potatoes per plant higher than that of a non-transformed potato plant cultivated under the same conditions, comprising introducing a gene encoding maize Dof 1 into the potato plant, and expressing said gene.

2. A method for producing a potato plant which bears potatoes, wherein said plant has a starch content in the tuber higher than that of a non-transformed potato plant cultivated under the same conditions, comprising introducing a gene encoding maize Dof 1 into the potato plant, and expressing said gene.

3. A method for producing a potato plant which bears potatoes wherein said plant has a starch content per plant higher than that of a non-transformed potato plant cultivated under the same conditions, comprising introducing a gene encoding maize Dof 1 into the potato plant, and expressing said gene.

4. A method for producing starch comprising cultivating a potato plant which bears potatoes, wherein said plant has a tuber yield of potatoes per plant higher than that of a non-transformed potato plant cultivated under the same conditions, and wherein said potato plant has been transformed with a gene encoding maize Dof 1, and isolating starch from the yielded tubers.

5. A potato plant comprising a tuber part and a leaf part, wherein said tuber yield is higher than that of a non-transformed potato plant, wherein a gene encoding maize Dof 1 is introduced into the potato plant.

6. The method of claim 1, wherein the maize Dof 1 comprises the amino acid sequence of SEQ ID No. 2.

* * * * *

SEQUENCE LISTING

<160> NUMBER OF SEQ ID NOS: 6

<210> SEQ ID NO 1
<211> LENGTH: 717
<212> TYPE: DNA
<213> ORGANISM: Zea mays
<220> FEATURE:
<223> OTHER INFORMATION: Dof1 gene sequence

<400> SEQUENCE: 1
atgcaggagg cgtcatcggc ggcggcggcg ggggccgagc ccggccgtcg ggcggcgcag    60

-continued

```
catcagttcg ccggcgtgga cctccggcgg cccaaggggt acgcggcgcc ggcgccggcg    120
ccggcggtgg gcgaggggga cccgtgcccg cggtgtgcgt cgcgggacac caagttctgc    180
tactacaaca actacaacac ctcccagccg cgccacttct gcaagggctg ccgccgctac    240
tggaccaagg gtggcacgct gcgcaacgtc cccgtcggcg gcggcacccg caagaagccc    300
tcctcctcct cctcgtcgtc gtcctacgtg gccgccgcgg acgccgacag gcagcccaag    360
aagaagcccg ccagcaagaa gcgccgcgtc gtggcgccgg ccccggagct cgccaccgcg    420
gccgacccag caagacggc gaccaccacc acgacgacga gcgagatcac cacggagact     480
ggcgcgctgg aggactccga ctccctggcg cacctgctgc tgcagcccgg gacagaggac    540
gcggaggccg tcgcgctcgg cctcggcctc tccgacttcc cctccgcgg gaaggcggtg     600 ctggacgacg aggactcgtt cgtgtggccc gccgcgtcgt tcgacatggg cgcgtgctgg    660
gccggcgcag ggttcgccga cccggacccc gcctgcatct tcctcaacct cccgtga       717
```

```
<210> SEQ ID NO 2
<211> LENGTH: 238
<212> TYPE: PRT
<213> ORGANISM: Zea mays
<220> FEATURE:
<223> OTHER INFORMATION: Dof1 protein sequence

<400> SEQUENCE: 2
```

```
Met Gln Glu Ala Ser Ser Ala Ala Ala Gly Ala Glu Pro Gly Arg
1               5                   10                  15

Arg Ala Ala Gln His Gln Phe Ala Gly Val Asp Leu Arg Arg Pro Lys
            20                  25                  30

Gly Tyr Ala Ala Pro Ala Pro Ala Pro Ala Val Gly Glu Gly Asp Pro
        35                  40                  45

Cys Pro Arg Cys Ala Ser Arg Asp Thr Lys Phe Cys Tyr Tyr Asn Asn
    50                  55                  60

Tyr Asn Thr Ser Gln Pro Arg His Phe Cys Lys Gly Cys Arg Arg Tyr
65                  70                  75                  80

Trp Thr Lys Gly Gly Thr Leu Arg Asn Val Pro Val Gly Gly Gly Thr
                85                  90                  95

Arg Lys Lys Pro Ser Ser Ser Ser Ser Ser Ser Tyr Val Ala Ala
            100                 105                 110

Ala Asp Ala Asp Arg Gln Pro Lys Lys Lys Pro Ala Ser Lys Lys Arg
        115                 120                 125

Arg Val Val Ala Pro Ala Pro Glu Leu Ala Thr Ala Ala Asp Pro Gly
    130                 135                 140

Lys Thr Ala Thr Thr Thr Thr Thr Ser Glu Ile Thr Thr Glu Thr
145                 150                 155                 160

Gly Ala Leu Glu Asp Ser Asp Ser Leu Ala His Leu Leu Gln Pro
                165                 170                 175

Gly Thr Glu Asp Ala Glu Ala Val Ala Leu Gly Leu Gly Leu Ser Asp
            180                 185                 190

Phe Pro Ser Ala Gly Lys Ala Val Leu Asp Asp Glu Asp Ser Phe Val
        195                 200                 205

Trp Pro Ala Ala Ser Phe Asp Met Gly Ala Cys Trp Ala Gly Ala Gly
    210                 215                 220

Phe Ala Asp Pro Asp Pro Ala Cys Ile Phe Leu Asn Leu Pro
225                 230                 235
```

```
<210> SEQ ID NO 3
<211> LENGTH: 26
<212> TYPE: DNA
<213> ORGANISM: Artificial
<220> FEATURE:
<223> OTHER INFORMATION: PCR primer for amplification of Dof1 gene
      contained in vector

<400> SEQUENCE: 3
ttccattgcc cagctatctg tcactt                                          26

<210> SEQ ID NO 4
<211> LENGTH: 26
<212> TYPE: DNA
<213> ORGANISM: Artificial
<220> FEATURE:
<223> OTHER INFORMATION: PCR primer for amplification of NPTII gene
      contained in vector

<400> SEQUENCE: 4
tcatcgcaag accggcaaca ggattc                                          26

<210> SEQ ID NO 5
<211> LENGTH: 21
<212> TYPE: DNA
<213> ORGANISM: Artificial
<220> FEATURE:
<223> OTHER INFORMATION: PCR primer for amplification of NPTII gene
      contained in vector

<400> SEQUENCE: 5
cccctcggta tccaattaga g                                               21

<210> SEQ ID NO 6
<211> LENGTH: 24
<212> TYPE: DNA
<213> ORGANISM: Artificial
<220> FEATURE:
<223> OTHER INFORMATION: PCR primer for amplification of NPTII gene
      contained in vector

<400> SEQUENCE: 6 cgggggtgg gcgaagaact ccag                                             24
```